(12) United States Patent
Yu et al.

(10) Patent No.: US 7,260,427 B2
(45) Date of Patent: *Aug. 21, 2007

(54) METHOD AND APPARATUS FOR DETERMINING THE CORONARY SINUS VEIN BRANCH ACCESSED BY A CORONARY SINUS LEAD

(75) Inventors: Yinghong Yu, Maplewood, MN (US); Jiang Ding, Maplewood, MN (US); Jeng Mah, Shoreview, MN (US); Julio Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 243 days.

This patent is subject to a terminal disclaimer.

(21) Appl. No.: 10/729,301

(22) Filed: Dec. 5, 2003

(65) Prior Publication Data

US 2004/0116975 A1 Jun. 17, 2004

Related U.S. Application Data

(62) Division of application No. 09/822,638, filed on Mar. 30, 2001, now Pat. No. 6,705,999.

(51) Int. Cl.
*A61B 5/0452* (2006.01)
(52) U.S. Cl. .......................................... 600/509; 607/27
(58) Field of Classification Search ........ 600/508–510; 607/9, 27, 28
See application file for complete search history.

(56) References Cited

U.S. PATENT DOCUMENTS 3,768,487 A * 10/1973 Rose ............................ 607/27
4,458,691 A 7/1984 Netravali
5,469,858 A 11/1995 Osborne
5,544,661 A 8/1996 Davis et al.
5,634,469 A 6/1997 Bruder et al.
5,694,942 A 12/1997 Escalona
5,740,808 A 4/1998 Panescu et al.
5,827,196 A 10/1998 Yeo et al.
6,115,630 A 9/2000 Stadler et al.
6,144,880 A 11/2000 Ding et al.
6,705,999 B2 3/2004 Yu et al.
6,766,189 B2 7/2004 Yu et al.
6,993,389 B2 1/2006 Ding et al.
2004/0162496 A1 8/2004 Yu et al.
2005/0216065 A1 9/2005 Ding et al.

* cited by examiner

*Primary Examiner*—Scott M. Getzow
(74) *Attorney, Agent, or Firm*—Schwegman, Lundberg, Woessner & Kluth, P.A.

(57) ABSTRACT

Systems and methods for determining the coronary sinus vein branch location of a left ventricle electrode are disclosed. The systems and methods involve detecting the occurrence of electrical events within the patient's heart including sensing one or more of the electrical events with the electrode and then analyzing the electrical events to determine the electrode's position. The determination of electrode position may be used to automatically adjust operating parameters of a VRT device. Furthermore, the determination of electrode position may be made in real-time during installation of the electrode and a visual indication of the electrode position may be provided on a display screen.

21 Claims, 7 Drawing Sheets

METHOD AND APPARATUS FOR DETERMINING THE CORONARY SINUS VEIN BRANCH ACCESSED BY A CORONARY SINUS LEAD

This application is a divisional of application Ser. No. 09/822,638, filed Mar. 30, 2001, now U.S. Pat. No. 6,705,999 which application(s) are incorporated herein by reference.

TECHNICAL FIELD

The present invention relates to ventricular resynchronization therapy (VRT) devices. More specifically, the present invention relates to determining a coronary vein branch position of the coronary sinus lead of a VRT device.

BACKGROUND

Ventricular resynchronization therapy is one method of treating heart failure patients. VRT often requires that the left ventricle of a patient be electrically stimulated. This is especially true if there is a conduction disorder in the left ventricle of the heart whereby the fast conductivity fibers (i.e., pumping system) in the left ventricle are damaged. When the conduction fibers are damaged, electrical waves traveling through the heart no longer travel quickly through the high speed fibers but instead travel much slower as they pass sequentially through muscle conduction. This slowing of the wave propagation through the left ventricle may cause one part (usually the septum) of the ventricle to contract first and begin to relax before another part (usually the freewall) of the ventricle contracts.

One scenario is that the freewall of the ventricle tends to expand during the period of contraction of the septum. Once the freewall begins to contract, the septum has relaxed. As a result of the septum and freewall portions contracting at different times, blood is passed side-to-side within the ventricle rather than being efficiently pumped out into the arteries.

VRT attempts to improve the pumping efficiency of the heart by providing an electrical stimulation to a later contracting part of the ventricle, for example the freewall, contemporaneously with the natural contraction of the earlier contracting portion, such as the septum. Because both sides contract at approximately the same time with VRT, the volume of the left ventricle is significantly reduced and blood is effectively pumped out into the arteries. To provide such electrical stimulation, an electrode connected to a VRT device must be positioned near the delayed region of the ventricle. The delayed region may be accessed via a branch of the coronary sinus vein that extends over the portions of the left ventricle.

The most accessible branches of the coronary sinus vein include the lateral, posterior, and anterior branches. Creating an electrical stimulation in the lateral or posterior branch provides the best hemodynamic response and maximizes the benefit from VRT for patients with left ventricle conduction disorder. Therefore, it is desirable to place the electrode of the VRT device in the lateral or posterior branch instead of the anterior branch. Furthermore, the timing of the electrical impulse provided by the VRT device to the electrode must be set according to the position of the electrode to induce contraction of the delayed portion of the ventricle at the appropriate time. Thus, the location of the electrode must be known.

During installation of the electrode, fluoroscopy is used to determine the position of the lead, and fluoroscopy exposes the patient to X-ray radiation. If the patient has an abnormal coronary sinus vein system, then fluoroscopy may become unreliable in determining the location of the electrode. Additionally, unusual anatomy may require a longer fluoroscopy exposure time. Thus, using fluoroscopy to determine electrode position during installation has drawbacks.

Thus, it is desirable to provide a method and system that enables the position of the electrode in the left ventricle to be determined without or in addition to fluoroscopy, to automatically configure the VRT device based on the detected position, and to display in real-time the detected position on a video display.

SUMMARY

Embodiments of the present invention assist in installation and/or setup and identification of an electrode in the left ventricle area of a patient's heart. These embodiments involve detecting electrical events in the patient's heart and then determining the position of the left ventricle (LV) electrode from measurements of the electrical events.

The present invention may be viewed as a method for determining a position of a first electrode placed within a left ventricle area of a patient's heart. The method involves detecting a first depolarization event within the heart and sensing, with the first electrode, a second depolarization event within the heart. The method further involves measuring a first interval between the first depolarization event and the second depolarization event and determining from at least the first interval whether the lead has a lateral/posterior position or an anterior position within the left ventricle.

The present invention may be viewed as another method for determining a position of an electrode within a left ventricle of a patient's heart. This method involves detecting a first depolarization event within the heart and sensing, with the electrode, a second depolarization event within the heart. The method also involves measuring a first interval between the first depolarization event and the second depolarization event and detecting a third depolarization event within the heart. A second interval is measured between the third depolarization event and the second depolarization event, and the electrode position is determined based on an evaluation of the first and the second intervals.

The present invention may be viewed as a system for determining the position of a first electrode in a left ventricle area of a patient's heart. The system includes one or more detection devices for detecting at least first and second electrical events in the patient's heart, one of the one or more detection devices being electrically connected to the first electrode and detecting the second electrical event in the left ventricle area. The system also includes a processing device in electrical communication with the one or more detection devices. The processing device is configured to calculate a first interval between the first and second electrical events and determine the position of the electrode based at least upon the first interval.

The present invention may be viewed as another system for determining the position of a first electrode in a left ventricle area of a patient's heart. This system includes means for detecting a first electrical event within the patient's heart, means for detecting a second electrical event occurring at the first electrode, and means for determining whether the first electrode has an anterior or lateral/posterior position within the left ventricle based at least on a first interval between the first and second electrical events.

The present invention may be viewed as a method for assisting installation of an electrode in a left ventricle of a patient's heart. This method involves placing the electrode in a coronary sinus vein branch of the left ventricle and detecting a plurality of electrical events in the patient's heart during a heart beat, wherein at least one of the plurality of electrical events is sensed by the electrode. The method also involves determining from the plurality of electrical events whether the electrode has an anterior or a lateral/posterior vein branch position during the heart beat and displaying on a display screen an indication of the determined position of the electrode.

The present invention may be viewed as a method for assisting installation of an electrode of a VRT device in a left ventricle of a patient's heart. The method involves placing the electrode in a coronary sinus vein branch of the left ventricle and detecting a plurality of electrical events in the patient's heart during a heart beat, wherein at least one of the plurality of electrical events is sensed by the electrode. The method also involves determining from the plurality of electrical events whether the electrode has an anterior or a lateral/posterior vein branch position during the heart beat and adjusting settings used by the VRT device based upon the determined position of the electrode.

DETAILED DESCRIPTION

Figure 1:
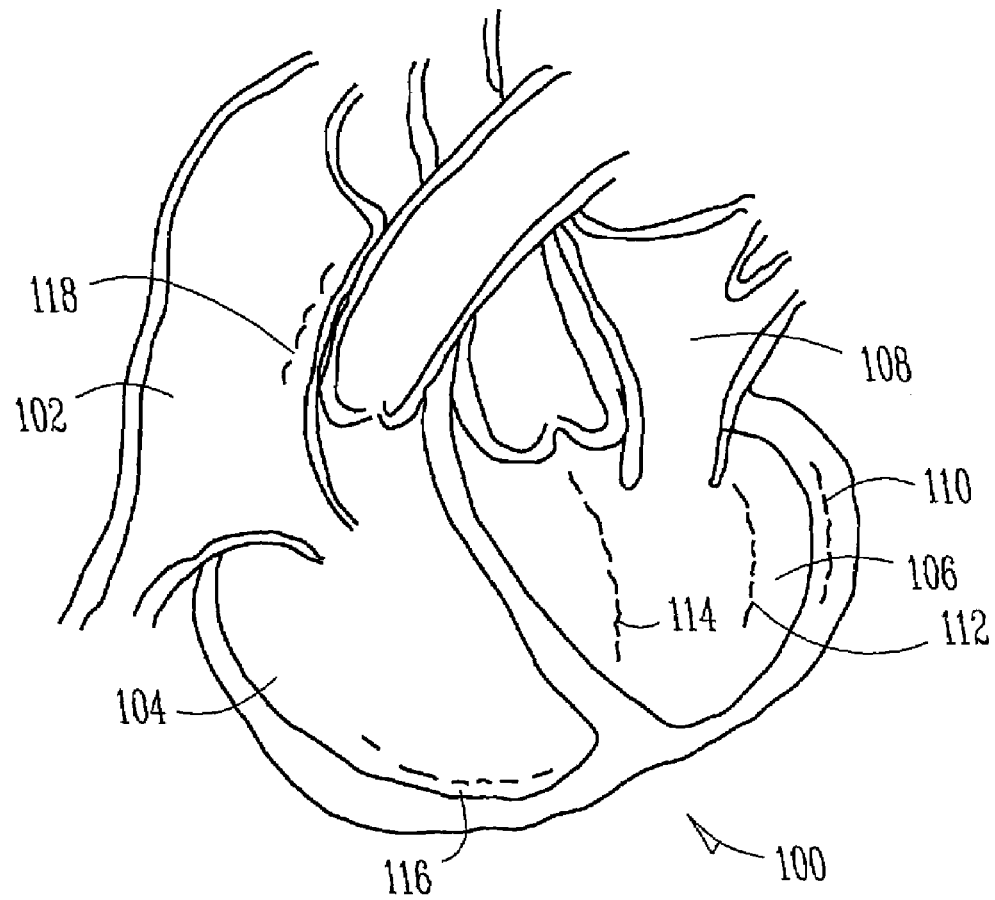
FIG. 1 illustrates a typical human heart with locations for placement of electrical leads in accordance with embodiments of the present invention.

Various embodiments of the present invention will be described in detail with reference to the drawings, wherein like reference numerals represent like parts and assemblies through the several views. Reference to various embodiments does not limit the scope of the invention, which is limited only by the scope of the claims attached hereto.

Embodiments of the present invention assist in the installation and/or setup of an electrode in the coronary sinus vein branches of the left ventricle area of a patient's heart. These embodiments provide systems and methods that may be used in place of or as a supplement to fluoroscopy. Furthermore, certain of these embodiments provide methods and systems for providing automatic adjustment of VRT settings that are based on the electrode position and are necessary for proper stimulation of the left ventricle. Certain of these embodiments also provide methods and systems for providing real-time indication of the electrode position during electrode installation to assist in providing the most beneficial placement of the electrode.

FIG. 1 illustrates a typical human heart 100. The heart 100 has four chambers including a right atrium area 102, a left atrium area 108, a right ventricle area 104, and a left ventricle area 106. Operation of VRT devices typically requires placement of an electrode in an atrium area such as 118. An electrode is also typically placed in a right ventricle apex area such as 116. Embodiments of the present invention are directed to determining the placement of an electrode in the left ventricle area.

The electrode for the left ventricle area is generally inserted through the coronary sinus vein into one of the three most accessible branches spanning the surface of the ventricle including the anterior branch, the posterior branch, and the lateral branch. The anterior branch typically spans the anterior area 114. For patients with a left bundle branch disorder which affects the conduction to the freewall of the left ventricle, placing the electrode in this anterior area 114 is least beneficial because it lies too closely to the septum of the left ventricle 106 and does not most effectively enhance the coordination of the left ventricle's contractions.

The posterior branch of the coronary sinus vein spans posterior area 112. Placing the electrode in this area allows the left ventricle freewall to be efficiently contracted in coordination with the contractions of the septum. The lateral branch of the coronary sinus vein spans lateral area 110. As with the posterior position, placing the electrode in the lateral area allows the freewall of the left ventricle 106 to be efficiently contracted in coordination with the septum as well. Thus, it is desirable to place the electrode in the posterior area 112 or the lateral area 110. These areas will be referred to together as the lateral/posterior position.

Figure 2:
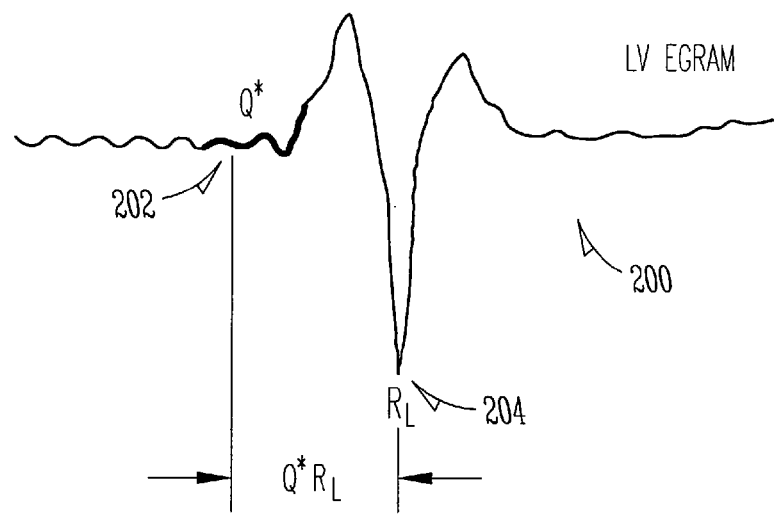
FIG. 2 shows an intracardiac electrogram measured by an electrode within the left ventricle and a $Q^*R_L$ interval measurement.

Embodiments of the present invention require detection of electrical events within the heart. Thus, the electrodes placed into the heart, including the electrode in the coronary sinus vein branch, sense the naturally occurring depolarization of the cells as the electrical wave travels by the electrode as it moves down the surface of the heart from the atrium area to the ventricle area. FIG. 2 shows an intracardiac electrogram signal 200 of the left ventricle that is sensed by the electrode being inserted through the coronary sinus vein. As the electrical activation begins in the ventricle, the electrode senses an electrical depolarization event such as onset (Q*) 202 of the QRS complex. The QRS complex is the electrical depolarization activity that occurs in the ventricles of the heart as the electrical wave propagates through the ventricles. After the onset (Q*) 202, the when the electrical wave passes by the electrode, another electrical depolarization event such as the peak ($R_L$) 204 of the QRS complex is sensed. Alternatively, the maximum negative derivative of the R wave may be sensed in place of the peak value.

The electrode being inserted into the left ventricle area senses an electrogram signal 200 of FIG. 2 regardless of whether it is positioned in the anterior or lateral/posterior position. However, the interval (Q*$R_L$) between the onset (Q*) 202 and the peak ($R_L$) 204 changes depending upon the electrode's position because the time of sensing the onset (Q*) 202 is not significantly affected by the position of the electrode but the time of sensing the peak ($R_L$) 204 is so affected. The interval (Q*$R_L$) is smaller if the electrode lies in the anterior position than it is if the electrode lies in the lateral/posterior position. Therefore, this interval may be computed and relied upon to determine the electrode's position.

Figure 3:
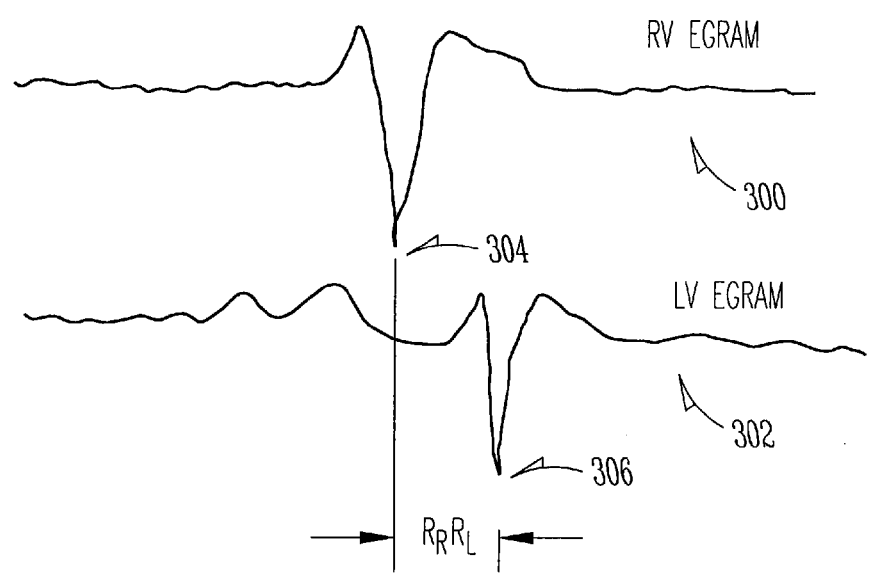
FIG. 3 shows an intracardiac electrogram measured by an electrode within the right ventricle in relation to an intracardiac electrogram measured on the same beat by an electrode within the left ventricle and an $R_R R_L$ interval measurement.

FIG. 3 shows an intracardiac electrogram signal 300 sensed by an electrode placed in a right ventricle location 116 in relation to the intracardiac electrogram signal 302 sensed by the left ventricle electrode. The right ventricle electrode senses an electrical depolarization event such as the peak ($R_R$) 304 of the QRS complex as the electrical wave passes by. The occurrence of this peak ($R_R$) 304 is not affected by the placement of the left ventricle electrode, but the occurrence of the QRS complex peak ($R_L$) 306 is affected by the placement. Therefore, this peak ($R_R$) 304 may be used as a reference point for measuring the relative timing of the peak ($R_L$) 306 of the QRS complex detected by the left ventricle electrode. The interval ($R_R R_L$) between the two peaks may also be computed and relied upon to determine the electrode's position.

A-wave electrical depolarization activity (A) detected by an electrode in the atrium area such as 118 is also unaffected by the placement of the left ventricle electrode. Therefore, A-wave activity detected by the atrial electrode may also be used as a reference marker for determining the timing of the left ventricle electrode sensing the peak $R_L$ of the QRS complex. However, because the delay from the transition of the electrical wave from the atrium area to the ventricle area (A/V delay) may significantly vary from one patient to the next, it is generally not as accurate to determine left ventricle (LV) electrode position based on an interval (A $R_L$) measured from the occurrence of atrial activity (A) to the occurrence of the peak ($R_L$) 306 of the QRS complex detected by the left ventricle electrode.

Whether using the interval (Q*$R_L$), the interval ($R_R R_L$), or the interval (A $R_L$), the position of the electrode may be detected by comparing the interval to a threshold value determined empirically. It has been found that 100 ms and shorter Q*$R_L$ intervals generally indicate an anterior position in humans. It has also been found that 50 ms and shorter $R_R R_L$ intervals generally indicate an anterior position in humans. Rather than using a single interval, both the interval (Q*$R_L$) and the interval ($R_R R_L$) may be computed and used to determine lead position. The sum of both intervals may be compared to a threshold, such as 150 ms for humans where 150 ms and shorter interval sums indicate an anterior position. Alternatively, both intervals may be statistically combined to find the probability of the electrode being in the anterior or the lateral/posterior position. It has been empirically determined that in human's, the following equations provide a reliable basis for determining position.

$$d_A = 0.004(Q^*R_L + R_R R_L - 100)^2,$$

$$d_L = 0.004(Q^*R_L + R_R R_L - 200)^2, \text{ and}$$

$$P = \frac{\exp(-0.5\ d_A)}{\exp(-0.5\ d_A) + \exp(-0.5\ d_L)} = \frac{1}{1 + \exp[-0.5(d_L - d_A)]}$$

where $d_A$ is the approximation of the probability density function of the electrode being in the anterior position, where $d_L$ is the approximation of the probability density function of the electrode being in the lateral/posterior position, where P is the probability of the electrode being in the anterior position, and where Q*$R_L$ and $R_R R_L$ values are in milliseconds.

The single parameter Q*$R_L$ may be used to determine electrode location with a probability classification rule, rather than a direct interval threshold comparison, such as where $$d_A = 0.001(Q^*R_L - 70)^2, \text{ and}$$

$$d_L = 0.001(Q^*R_L - 130)^2$$

with Q*$R_L$ expressed in milliseconds.

An anterior position is determined for a resulting probability value P of greater than or equal to 0.5.

The single parameter $R_R R_L$ may be used to determine electrode location with a probability classification rule, rather than a direct interval threshold comparison, such as where $$d_A = 0.0005(R_R R_L - 20)^2, \text{ and}$$

$$d_L = 0.0005(R_R R_L - 80)^2$$

with $R_R R_L$ expressed in milliseconds.

An anterior position is determined for a resulting probability value P of greater than or equal to 0.5.

For each of these probability classification rules, when P is equal to or greater than 0.5, then the position of the electrode is determined to be in an anterior position. Otherwise, the electrode is determined to be in the lateral/posterior position. Thus, the location of the electrode may be found by providing a device whose operations include sensing electrical events in the heart including an electrical event sensed by the LV electrode, measuring the intervals between the events, and then analyzing the intervals to find the electrode position.

The above-described classification rules based on the likelihood function P have been derived from a complex linear discriminant function that numerically maximizes the distance between the mean value from the Q*$R_L$ set and the mean value from the $R_R R_L$ set measured at implants from electrodes with known anterior and lateral/posterior positions. Electrode position was measured in 69 patients with 104 total electrode positions. Thirty-seven patients had a single set of interval measurements and the remaining 32 patients had interval measurements taken at different electrode positions.

The above-described classification rules were validated by randomly selecting one set of measurements per patient to form training data. The remaining sets of measurements formed the test data. Statistical discriminant analysis was used to analyze the training and test data in addition to using the classification rules for P. Table A below shows the overall sensitivity (classification of lateral/posterior position correctly) and specificity (classification of anterior position correctly) estimated by using the classification rule for P utilizing both the $Q^*R_L$ and the $R_R R_L$ parameters and estimated by using the statistical discriminant analysis after 10,000 iterations.

TABLE A

|  | Test data, classification rule for P | Training data, classification rule for P | Test data, discriminant analysis | Training data, discriminant analysis |
| --- | --- | --- | --- | --- |
| Sensitivity | 80.7% | 76.9% | 79.4% | 77.6% |
| Specificity | 90.9% | 92.0% | 90.6% | 89.1% |

It can be seen from the cross-validation that the classification rule for P based on both the $Q^*R_L$ and the $R_R R_L$ parameters can determine electrode position. The accuracy of the classification rule above for P is comparable to that obtained by regular discriminant analysis, as indicated by Table A.

Table B shows the results of using the same patients and measurements while applying the single parameter $Q^*R_L$ classification rule. The accuracy of the classification rule is comparable to that obtained by regular discriminant analysis.

TABLE B

|  | Test data, 100 ms threshold classification rule | Training data, 100 ms threshold classification rule | Test data, discriminant analysis | Training data, discriminant analysis |
| --- | --- | --- | --- | --- |
| Sensitivity | 77.9% | 78.0% | 77.3% | 76.0% |
| Specificity | 88.2% | 84.3% | 90.9% | 86.8% |

Table C shows the results of using the same patients and measurements while applying the single parameter $R_R R_L$ classification rule. The accuracy of this classification rule is also comparable to that obtained by regular discriminant analysis.

TABLE C

|  | Test data, 50 ms threshold classification rule | Training data, 50 ms threshold classification rule | Test data, discriminant analysis | Training data, discriminant analysis |
| --- | --- | --- | --- | --- |
| Sensitivity | 80.8% | 76.9% | 82.1% | 77.8% |
| Specificity | 90.8% | 92.1% | 90.9% | 92.0% |

The probability classification rules mentioned above have been designed to produce the probability of the electrode having an anterior position. The probability classification rule could be altered so as to produce the probability of the electrode having a lateral/posterior position instead by replacing $d_A$ in the numerator with $d_L$. However, a lateral/posterior position would be concluded only where P is greater than 0.5 and an anterior position would be concluded where P is 0.5 or less. It is desirable to conclude that the electrode is in an anterior position when P=0.5, for either definition of P, to be cautious.

The embodiments of the operations of the invention utilizing detection of electrical events and threshold or classification rule comparisons described herein, such as but not limited to those of FIGS. 4–8, are implemented as logical operations in the system. The logical operations are implemented (1) as a sequence of computer implemented steps running on a computer system, such as a device programmer or the implantable or external VRT device itself, comprising a processing module and/or (2) as interconnected machine modules running within the computing system.

This implementation is a matter of choice dependent on the performance requirements of the computing system implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

Figure 4:
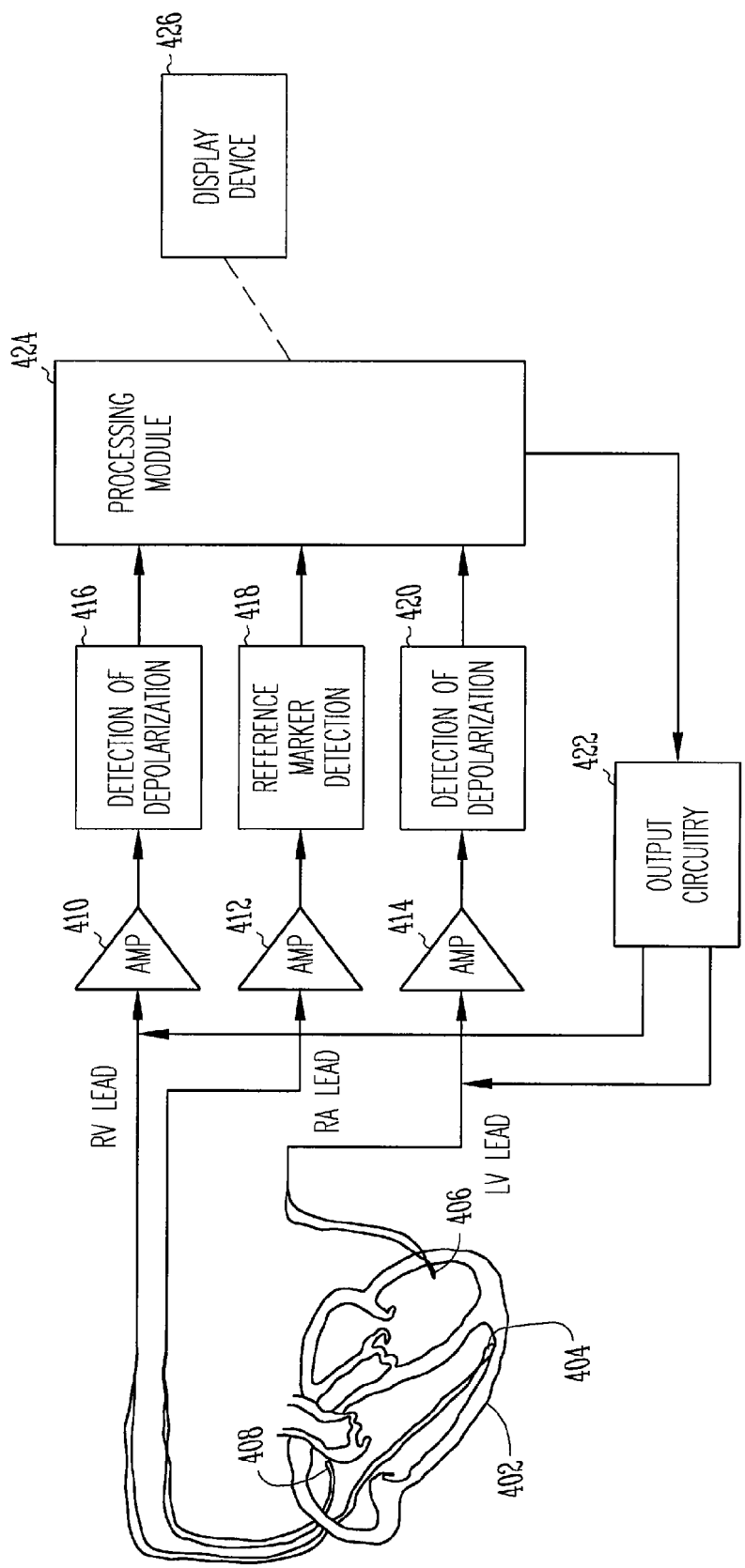
FIG. 4 depicts electrical lead and electrode placement within the heart and detection of the intracardiac electrogram signals from the electrodes.

FIG. 4 shows the configuration of the electrodes and electrical leads transferring signals from the electrodes to amplification, detection, and processing modules as would be the case during installation of the LV electrode 406. FIGS. 5–8 show exemplary processing operations of the processing module 424 that operate in conjunction with the configuration shown in FIG. 4. The heart 402 of FIG. 4 has an atrial electrode 408, a right ventricle (RV) electrode 404, and an LV electrode 406. The LV electrode 406 may be in the process of being installed by a surgeon while the operations of FIGS. 4–8 are occurring.

The atrial electrode 408 has leads connected to an amplifier 412 that boosts the signal sensed by the electrode to improve the signal to noise ratio before the signal is provided to reference marker detection module 412. The RV electrode 404 has leads connected to an amplifier 410 that boosts its signal before being provided to depolarization detection module 416. The LV electrode 406 has leads connected to an amplifier 414 that boosts its signal before being provided to depolarization detection module 420.

Reference marker detection module 412 may utilize existing circuitry in a VRT device or a VRT device programmer telemetered to the VRT device to detect the A-wave reference activity (A). Detection module 416 may utilize existing peak detector circuitry in a VRT device or VRT device programmer to detect the peak ($R_R$) of the QRS complex at the RV electrode 402. Likewise, detection module 420 may utilize existing peak detector circuitry in a VRT device or VRT device programmer to detect the peak ($R_L$) of the QRS complex at the LV electrode 406. If the QRS complex onset ($Q^*$) as sensed by the LV electrode is to be used, the waveform including the QRS complex must be acquired and analyzed, such as by the detection module 420 of the VRT device or VRT device programmer. The values determined by the detection modules are passed to the processing module 424 for analysis.

The acquisition involves digitizing the waveform including the activity beginning at the time of the atrial reference marker and extending beyond the QRS complex received by the LV electrode 406 and storing it in memory of the VRT device or VRT device programmer. Then, the processing module may find Q such as by the following process.

First, the detection module 420 smooths the waveform V(n). This may be done by smoothing the waveform V(n) seven times using a 5 point rectangular moving window (for a sampling frequency of 500 Hz) whereby the 5 samples for each window are averaged and the average is assigned to the middle sample of the five. A derivative dV(n)/dt of the smoothed waveform is taken, and the absolute value of the derivative dV(n)/dt is normalized to range from 0 to 1.

The time samples n from the atrial reference marker time $T_P$ to the time $T_R$ of the peak ($R_L$) of the R wave of the QRS complex are analyzed. This analysis involves calculating the mean and standard deviation of both the smoothed waveform V(n) and the normalized absolute value of its derivative dV(n)/dt for each time sample within a 50 ms moving window. The window with the minimum mean plus standard deviation for |dV(n)/dt| is found and its values are used in the following steps.

For each sample n between $T_P$ and $T_R$, if the mean for |dV(n)/dt| within this window is less than |dV(n)/dt|, and if |dV(n−1)/dt| is less than or equal to the mean for |dV(n)/dt|, then the number of data points N in another 50 ms window is found. N is the accumulation of each data point where |dV(nw)/dt| is greater than the mean of |dV(n)/dt| plus the standard deviation of |dV(n)/dt|. The window sample nw of this other window ranges from n to n plus the total number of data points in the window.

If N divided by the total number of data points in the window is greater than 0.96 and $T_q$=0, then set $T_q$ equal to n0−1, where $T_q$ is the current result of sample time for Q* and n0 is the time sample of the first data point that contributes to N. If the total number of data points in the window minus N is greater than or equal to 2, then $T_q$ is reset to zero. After this is completed for all values of n between $T_P$ and $T_R$, then the final value of $T_q$ is used as Q*. This process may be repeated to obtain a value of Q* for several beats, such as 16, and the median of these Q* values may be used in the above-mentioned classification rules. It may be desirable to include Q* values in the median determination for beats where the interval from R wave peak to R wave peak between beats has a variation within 10%.

Figure 5:
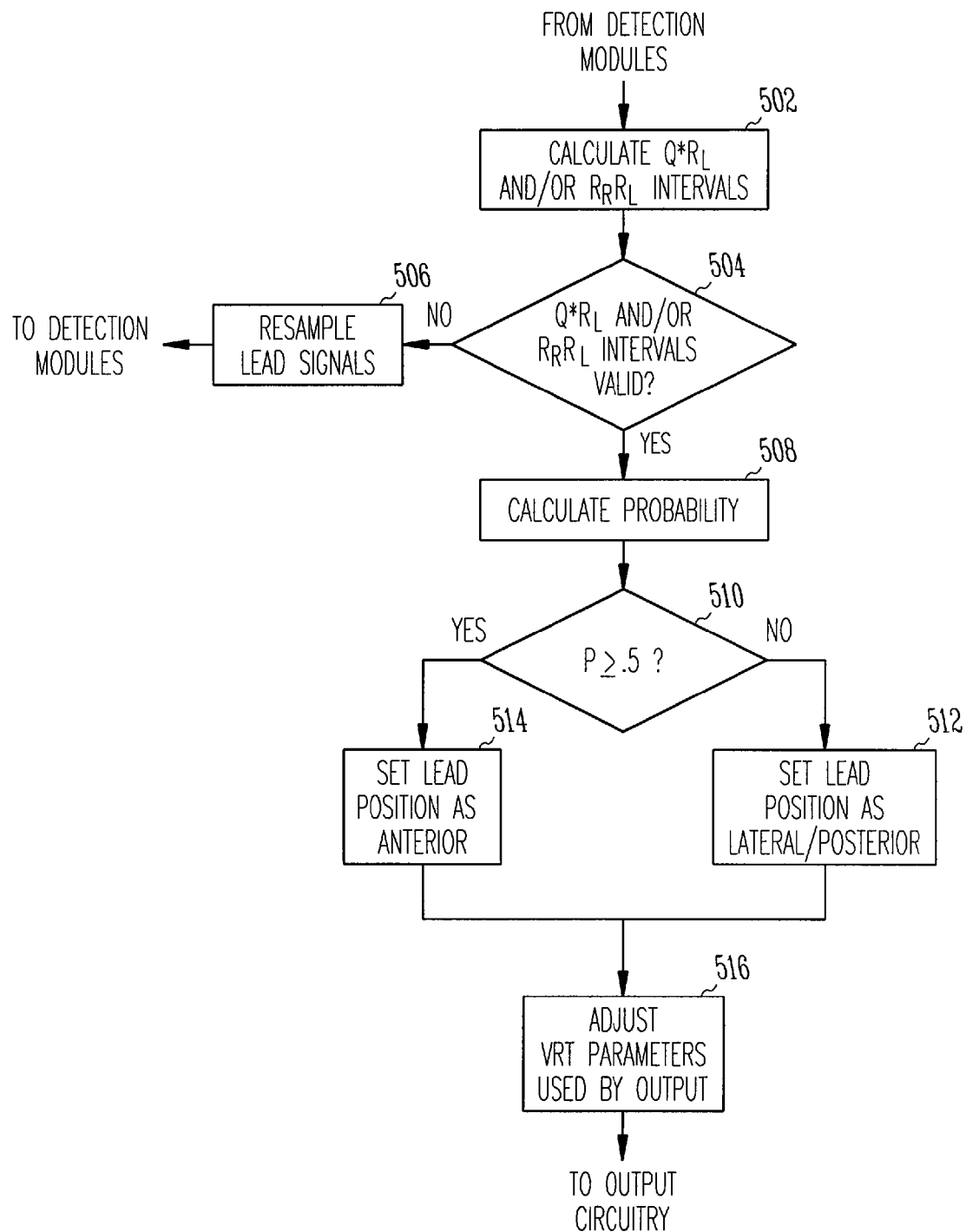
FIG. 5 illustrates the operational flow of an embodiment of the present invention where the VRT device settings are automatically adjusted in response to determination of electrode position within the left ventricle using one or more interval measurements and a probability rule.
Figure 7:
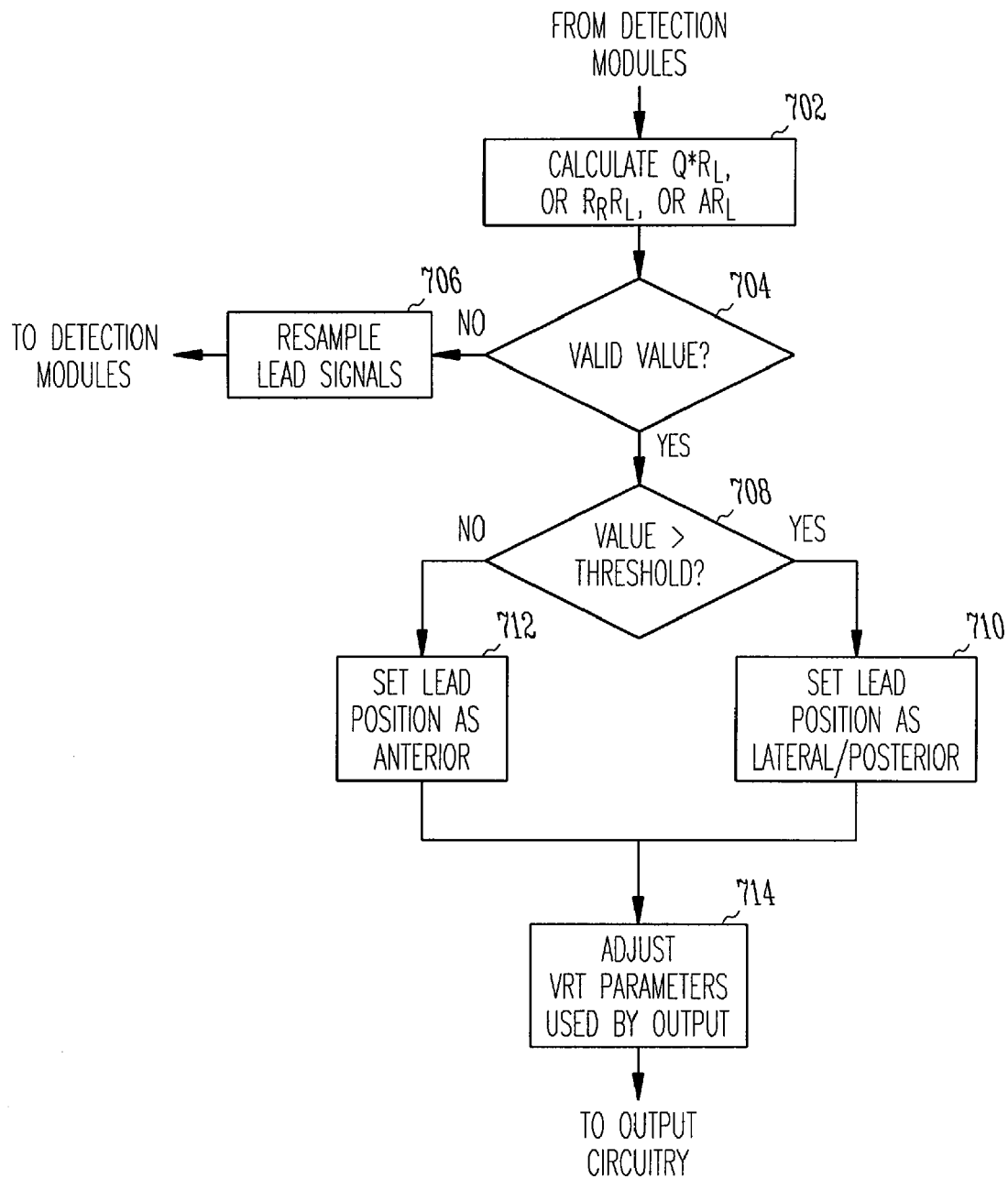
FIG. 7 shows the operational flow of an embodiment of the present invention where the VRT device settings are automatically adjusted in response to determination of electrode position within the left ventricle using single or multiple interval threshold comparison.

In certain embodiments, the output circuitry module 422 receives VRT settings as automatically determined by the processing module 424 from operations such those as shown in FIGS. 5 and 7. Otherwise, output circuitry module 422 may receive VRT settings as entered manually after determination of the LV electrode position. The output circuitry module 422 provides timed electrical pulses to the electrical leads connected to the RV electrode 404 and the LV electrode 406 to cause these electrodes to stimulate the ventricles at specified times during normal operation. The video display 426 receives signals from the processing module 424 that cause the video display 426 to display an indication of LV electrode position that can be viewed by the surgeon in real-time.

FIG. 5 illustrates one example of the processing operations of processing module 424 that receives the detection of electrical events in the heart from detection modules of FIG. 4 to automatically set the VRT device for proper operation based on the LV electrode position. This example may utilize the previously discussed statistical combination of the interval (Q*$R_L$) and the interval ($R_R$ $R_L$), or it may utilize a single interval. At calculate operation 502, the interval (Q*$R_L$) and/or the interval ($R_R$ $R_L$) are calculated from values found by the detection operations 416 and 420. Query operation 504 then detects whether the two intervals are valid by comparison to standard limits for each. Thus, if either of the two intervals is too short or too long to be accurate, then resample operation 506 triggers the detection modules 416 and 420 to resample the electrical events for another measurement. Valid ranges for humans are approximately 0 to 500 ms for (Q*$R_L$) and −200 to 500 ms for ($R_R$ $R_L$).

If query operation 504 detects valid intervals, then probability operation 508 computes the values $d_A$, $d_L$, and P using a single interval or both. Computing P may involve mathematical application of the desired equation for P to the measured intervals or may involve looking up the value of P in a table stored in memory of the VRT device or programmer. Query operation 510 then tests whether P is greater than or equal to 0.5. If so and P is defined as the probability of anterior position, then position operation 514 sets the position in the VRT device and/or programmer as anterior. If query operation 510 detects that P is less than 0.5, then position operation 512 sets the position in the VRT or programmer as lateral/posterior. Based on setting the position as anterior or lateral/posterior, parameter operation 516 sets the VRT parameters such that the timing used by output circuitry module 422 to send a pulse to the LV electrode accounts for the LV electrode position.

Figure 6:
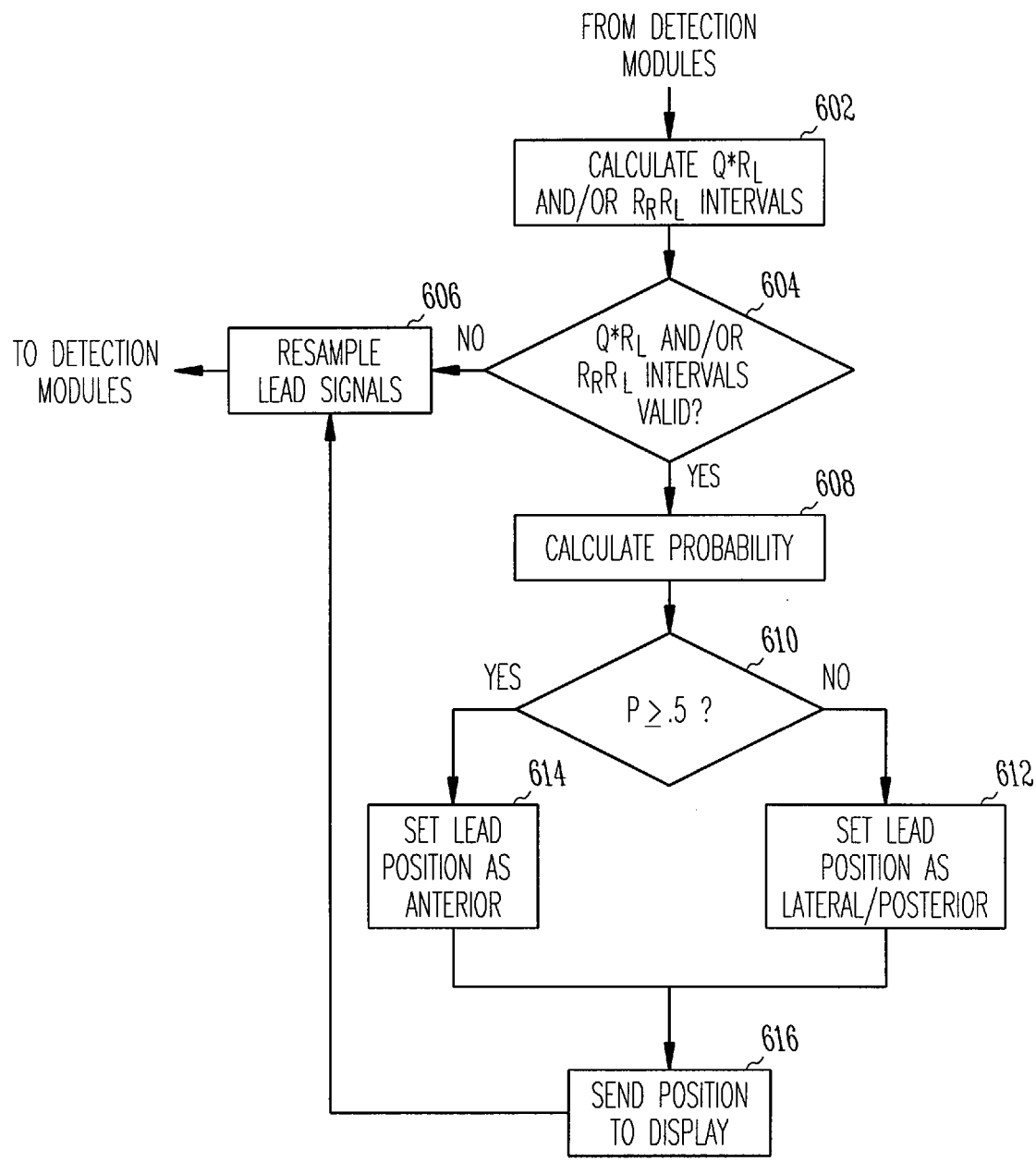
FIG. 6 depicts the operational flow of an embodiment of the present invention where the electrode position, determined using one or more interval measurements and a probability rule, is provided to a display in real-time during the installation of the left ventricle electrode in the patient.

FIG. 6 illustrates an example of the processing operations of processing module 424 that receives the detection of electrical events in the heart from detection modules of FIG. 4 to provide a visual indication on a display screen of the LV electrode position. This visual display may be provided in real-time during installation of the LV electrode on a beat-by-beat basis. This example also utilizes the previously discussed statistical combination of the interval (Q*$R_L$) and the interval ($R_R$ $R_L$), or it may utilize a single interval. At calculate operation 602, the interval (Q*$R_L$) and/or the interval ($R_R$ $R_L$) are calculated from values found by the detection modules 416 and 420. Query operation 604 then detects whether the two intervals are valid by comparison to standard limits for each. Thus, if either of the two intervals is too short or too long to be accurate, then resample operation 606 triggers the detection modules 416 and 420 to resample the electrical events from another heart beat.

If query operation 604 detects valid intervals, then probability operation 608 computes the values $d_A$, $d_L$, and P, using a single interval or both. Query operation 610 then tests whether P is greater than or equal to 0.5. If so and P is defined as the probability of anterior position, then position operation 614 sets the position in the VRT device and/or programmer as anterior. If query operation 610 detects that P is less than 0.5, then position operation 612 sets the position in the VRT or programmer as lateral/posterior. Based on setting the position as anterior or lateral/posterior, display operation 616 sends a visual indication to a display screen 426 indicating the LV electrode position. The visual indication may be a display of the calculated intervals of operation 602 or it may simply indicate anterior or lateral/posterior. After updating the visual indicator at display operation 616, operational flow transitions to resample operation 606 where the detection modules of FIG. 4 sense the electrical events on the next heart beat and provide the detected values back to calculate operation 602 for another iteration.

FIG. 7 illustrates another example of the processing operations of processing module 424 that receives the detection of electrical events in the heart from detection modules of FIG. 4 to automatically set the VRT device for proper operation based on the LV electrode position. This example utilizes single or multiple interval threshold comparison where the value to compare against the threshold may be the interval (Q* $R_L$), the interval ($R_R$ $R_L$), the interval (A $R_L$), or a sum of two or all three intervals. At calculate operation 702, the desired interval(s) are calculated from values found by one or more of the detection operations 412, 416, and 420. Query operation 704 then detects whether the intervals are valid by comparison to standard limits for each. Thus, if any of the intervals is too short or too long to be accurate, then resample operation 706 triggers the detection modules 412, 416, and/or 420 to resample the electrical events from another heart beat.

If query operation 704 detects valid intervals, then query operation 708 tests whether the interval or sum of intervals exceeds the threshold stored in memory of the processing module 424. As mentioned, an empirically determined threshold that is reliable for humans is about 100 ms for ($Q^*R_L$) and 50 ms for ($R_R\ R_L$) or 150 ms if using the sum of both intervals for comparison to the threshold. If the threshold is not exceeded, then position operation 712 sets the position in the VRT device and/or programmer as anterior. If query operation 708 detects that the interval does exceed the threshold, then position operation 710 sets the position in the VRT or programmer as lateral/posterior. Based on setting the position as anterior or lateral/posterior, parameter operation 714 sets the VRT parameters such that the timing used by output circuitry module 422 to send a pulse to the LV electrode accounts for the LV electrode position.

Figure 8:
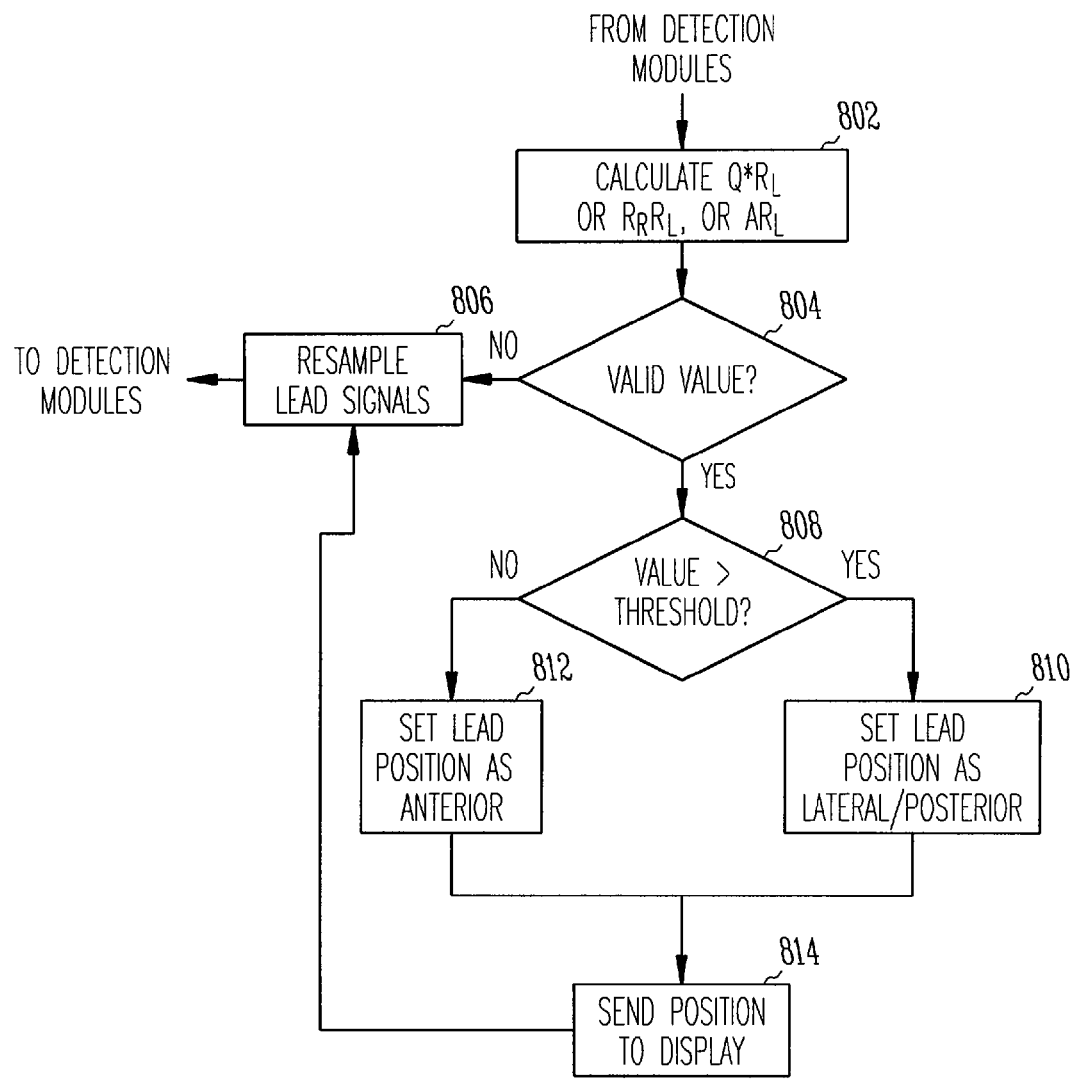
FIG. 8 depicts the operational flow of an embodiment of the present invention where the electrode position, determined using single or multiple interval threshold comparison, is provided to a display in real-time during the installation of the left ventricle electrode in the patient.

FIG. 8 illustrates another example of the processing operations of processing module 424 that receives the detection of electrical events in the heart from detection modules of FIG. 4 to provide a visual indication on a display screen of the LV electrode position. As with the operations of FIG. 6, this visual display may be provided in real-time during installation of the LV electrode on a beat-by-beat basis. This example utilizes single or multiple interval threshold comparison where the value to compare to the threshold may be the interval ($Q^*R_L$), the interval ($R_R\ R_L$), the interval ($A\ R_L$), or a combination thereof. At calculate operation 802, the desired interval is calculated from values found by one or more of the detection operations 412, 416, and 420. Query operation 804 then detects whether the two intervals are valid by comparison to standard limits for each. Thus, if either of the two intervals is too short or too long to be accurate, then resample operation 806 triggers the detection modules 412, 416, and/or 420 to resample the electrical events from another heart beat.

If query operation 804 detects valid intervals, then query operation 808 tests whether the interval exceeds the threshold stored in memory of the processing module 424. If not, then position operation 812 sets the position in the VRT device and/or programmer as anterior. If query operation 808 detects that the interval does exceed the threshold, then position operation 810 sets the position in the VRT or programmer as lateral/posterior. Based on setting the position as anterior or lateral/posterior, display operation 814 sends a visual indication to a display screen 426 indicating the LV electrode position. The visual indication may be a display of the calculated intervals of operation 802 or it may simply indicate anterior or lateral/posterior. After updating the visual indicator at display operation 816, operational flow transitions to resample operation 806 where the detection modules of FIG. 4 sense the electrical events on the next heart beat and provide the detected values back to calculate operation 802 for another iteration.

The operations of FIGS. 5 and 6 or 7 and 8 may be combined such that a real-time visual indication of the LV electrode position is shown on a display screen 426 and the VRT settings for output circuitry 422 are automatically adjusted based on the determined position. As mentioned, embodiments may employ the amplification, detection, and processing modules of FIG. 4 and operations of FIGS. 5-8 in an external VRT device, an implantable VRT device, or a VRT device programmer telemetered to the VRT device connected to the leads. Furthermore, embodiments may employ some of the modules and/or operations in the VRT device while employing others in the programmer.

Once the LV electrode is in a satisfactory position, as may have been determined by the surgeon viewing the display screen 426 while installing the LV electrode, the settings for the VRT device may be manually or automatically adjusted as discussed above. At that time, the processing operations of the present invention may terminate. The processing operations of the present invention may later be re-invoked to determine the LV electrode position or update the VRT settings in follow-up visits.

While the invention has been particularly shown and described with reference to preferred embodiments thereof, it will be understood by those skilled in the art that various other changes in the form and details may be made therein without departing from the spirit and scope of the invention.

We claim:

1. A method for assisting installation of an electrode in a left ventricle of a patient's heart, the method comprising the steps of:
   a. placing the electrode in a coronary sinus vein branch of the left ventricle;
   b. detecting a plurality of electrical events in the patient's heart during a heart beat, wherein at least one of the plurality of electrical events is sensed by the electrode; and
   c. determining from the plurality of electrical events whether the electrode has an anterior or a lateral/posterior vein branch position during the heart beat.

2. The method of claim 1, wherein the plurality of electrical events include an onset of a QRS complex at the electrode and a peak of the QRS complex at the electrode, wherein determining the vein branch position comprises computing an interval between the onset and the peak.

3. The method of claim 1, wherein the plurality of electrical events include a right ventricle QRS complex peak and left ventricle QRS complex peak at the electrode, wherein determining the vein branch position comprises computing an interval between the right ventricle QRS complex peak and the left ventricle QRS complex peak.

4. The method of claim 1, wherein the plurality of electrical events include atrial activity and a left ventricle QRS complex peak at the electrode, wherein determining the vein branch position comprises computing an interval between the atrial activity and the left ventricle QRS complex peak.

5. The method of claim 1, further comprising displaying on a screen an indication of said determined anterior or a lateral/posterior vein branch position of said electrode.

6. The method of claim 1, further comprising adjusting settings used by a VRT device based upon the determined position of the electrode.

7. The method of claim 2, further comprising dislaying on a screen an indication of said determined anterior or a lateral/posterior vein branch position of said electrode.

8. The method of claim 3,further comprising displaying on a screen an indication of said determined anterior or a lateral/position vein branch position of said electrode.

9. The method of claim 4, further comprising displaying on a screen an indication of said determined anterior or a lateral/posterior vein branch position of said electrode.

10. The method of claim 5, wherein the indication on the display screen includes displaying the interval and ranges for the interval for each vein branch position.

11. A system for assisting installation of an electrode in a left ventricle of a patient's heart, comprising:
one or more detection devices for detecting at least first and second electrical events in said patient's heart, one of said one or more detection devices being electrically connected to said electrode and detecting said second electrical event in the left ventricle; and
a processing device in electrical communication with said one or more detection devices, said processing device configured to calculate a first interval between said first and second electrical events and determining whether said electrode has a lateral/posterior position or an anterior position within the left ventricle of said patient's heart based at least upon said first interval.

12. The system of claim 11, wherein said first electrical event is atrial activity and said second electrical event is a peak of a QRS complex at said electrode.

13. The system of claim 11, wherein said first electrical event is an onset of a QRS complex and said second electrical event is a peak of a QRS complex at said electrode.

14. The system of claim 11, wherein said first electrical event is a peak of a right ventricle QRS complex occurring before or after the second electrical event and said second electrical event is a peak of a QRS at said electrode.

15. The system of claim 11, further comprising a second electrode that is adapted to be positioned in an atrium area of said patient's heart, one of said one or more detection devices being electrically connected to said second electrode and is adapted to detect said first electrical event in said atrium area prior to detection of said second electrical event, and wherein said second electrical event is a left ventricle QRS complex peak.

16. The system of claim 11, further comprising a second electrode that is adapted to be positioned in a right ventricle area of said patient's heart, one of said one or more detection deices being electrically connected to said second electrode and is adapted to detect said first electrical event in said right ventricle are before or after detection of said second electrical event, and wherein said first electrical event is a right ventricle QRS complex peak and said second electrical even is a left ventricle QRS complex peak.

17. The system of claim 11, wherein said electrode detects said first electrical event, said first electrical event being an onset of a left ventricle QRS complex, and wherein said second electrical event is a left ventricle QRS complex peak.

18. A method for assisting installation of an electrode in a left ventricle of a patient's heart, said method comprising:
placing said electrode in a coronary sinus vein branch of said left ventricle;
placing a second electrode in an atrium region or in a right ventricle area;
detecting a plurality of electrical events in said patient's heart during a heart beat, wherein at least one of said plurality of electrical events is sensed by said electrode;
determining from said plurality of electrical events whether said electrode has an anterior or a lateral/posterior vein branch position during said heart beat; and
displaying on a screen an indication of said determined anterior or a lateral/posterior vein branch position of said electrode wherein detecting said electrical events comprises detecting a first depolarization and a second depolarization event within said heart.

19. The method of claim 18, wherein determining whether said electrode has an anterior or a lateral/posterior vein branch position during said heart beat comprises:
measuring an interval between said first depolarization event and said second depolarization event; and
comparing said interval to a threshold and determining a lateral/posterior position when said interval is greater than said threshold.

20. The method of claim 18, wherein said first depolarization event is detected by sensing depolarization at said second electrode in said atrium region.

21. The method of claim 18, wherein said first depolarization event is detected by sensing a peak of a QRS complex at said second electrode in said right ventricle area.

* * * * *

UNITED STATES PATENT AND TRADEMARK OFFICE
CERTIFICATE OF CORRECTION

PATENT NO. : 7,260,427 B2 Page 1 of 1
APPLICATION NO. : 10/729301
DATED : August 21, 2007
INVENTOR(S) : Yu et al.

It is certified that error appears in the above-identified patent and that said Letters Patent is hereby corrected as shown below:

In column 12, lines 24-25, in Claim 1, after "comprising" delete "the steps of".

In column 12, line 26, in Claim 1, before "placing" delete "a.".

In column 12, line 28, in Claim 1, before "detecting" delete "b.".

In column 12, line 32, in Claim 1, before "determining" delete "c.".

In column 12, line 59, in Claim 7, delete "dislaying" and insert -- displaying --, therefor.

In column 12, line 62, in Claim 8, delete "3,further" and insert -- 3, further --, therefor.

In column 12, line 64, in Claim 8, after "lateral/" delete "position" and insert -- posterior --, therefor.

In column 13, line 39, in claim 16, delete "deices" and insert -- devices --, therefor.

Signed and Sealed this

Twenty-sixth Day of February, 2008

JON W. DUDAS
*Director of the United States Patent and Trademark Office*